US010827775B2

(12) United States Patent
Li et al.

(10) Patent No.: US 10,827,775 B2
(45) Date of Patent: Nov. 10, 2020

(54) NUTRITIONAL SUPPLEMENTS AFFECTING CARDIOVASCULAR EFFICIENCY

(71) Applicant: BEIJING GINGKO GROUP BIOLOGICAL TECHNOLOGY CO., LTD., Beijing (CN)

(72) Inventors: Yanmei Li, Beijing (CN); Lixin Ding, Beijing (CN)

(73) Assignee: BEIJING GINGKO GROUP BIOLOGICAL TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 16/337,223

(22) PCT Filed: Sep. 30, 2017

(86) PCT No.: PCT/CN2017/104837
§ 371 (c)(1),
(2) Date: Mar. 27, 2019

(87) PCT Pub. No.: WO2018/064966
PCT Pub. Date: Apr. 12, 2018

(65) Prior Publication Data
US 2019/0289892 A1    Sep. 26, 2019

Related U.S. Application Data

(60) Provisional application No. 62/404,853, filed on Oct. 6, 2016.

(51) Int. Cl.
| | | |
|---|---|---|
| A61K 36/00 | (2006.01) |
| A23L 33/105 | (2016.01) |
| A23L 33/15 | (2016.01) |
| A61K 36/05 | (2006.01) |
| A61K 36/82 | (2006.01) |
| A61K 31/728 | (2006.01) |
| A61K 31/12 | (2006.01) |
| A61K 31/352 | (2006.01) |
| A61P 9/00 | (2006.01) |
| A61K 9/48 | (2006.01) |
| A61K 31/7048 | (2006.01) |

(52) U.S. Cl.
CPC ............ *A23L 33/105* (2016.08); *A23L 33/15* (2016.08); *A61K 9/48* (2013.01); *A61K 31/12* (2013.01); *A61K 31/352* (2013.01); *A61K 31/7048* (2013.01); *A61K 31/728* (2013.01); *A61K 36/05* (2013.01); *A61K 36/82* (2013.01); *A61P 9/00* (2018.01); *A23V 2002/00* (2013.01); *A23V 2200/326* (2013.01); *A23V 2250/1944* (2013.01); *A23V 2250/211* (2013.01); *A23V 2250/2104* (2013.01); *A23V 2250/2112* (2013.01); *A23V 2250/21168* (2013.01); *A23V 2250/712* (2013.01)

(58) Field of Classification Search
None
See application file for complete search history.

(56) References Cited

U.S. PATENT DOCUMENTS

| | | |
|---|---|---|
| 2003/0008048 A1 | 1/2003 | Winston et al. |
| 2009/0047304 A1 | 2/2009 | Takahashi et al. |
| 2015/0290251 A1 | 10/2015 | Minatelli et al. |

FOREIGN PATENT DOCUMENTS

| | | | |
|---|---|---|---|
| CN | 101023963 A | | 8/2007 |
| CN | 101053409 A | | 10/2007 |
| CN | 104351807 A | | 2/2015 |
| CN | 104643100 A | | 5/2015 |
| CN | 105394749 A | | 3/2016 |
| CN | 105582001 A | | 5/2016 |
| JP | 2010043032 A | * | 2/2010 |
| JP | 2011063547 A | | 3/2011 |
| JP | 2014520165 A | | 8/2014 |
| JP | 2015110526 A | * | 6/2015 |
| JP | 2016073066 A | | 5/2016 |
| WO | 2006059730 A1 | | 6/2006 |

OTHER PUBLICATIONS

International Search Report with Written Opinion in corresponding international application No. PCT/CN2017/104837 dated Dec. 29, 2017 (10 pages).
Earnest et al.; "Effect of Astaxanthin on Cycling Time Trial Performance"; International Journal of Sports Medicine 32(11): pp. 882-884 (3 pages); Nov. 2011.
Extended European Search Report in corresponding European Application No. 17857847.2 dated Mar. 2, 2020 (9 pages).
Japanese Office Action in corresponding Japanese Application No. 2019-540483 dated May 12, 2020 (13 pages).
Earnest et al.; "Effect of Astaxanthin on Cycling Time Trial Performance"; International Journal of Sports Medicine; vol. 32, No. 11; pp. 882-888 (7 pages); Nov. 1, 2011.
Fassett et al; "Astaxanthin in Cardiovascular Health and Disease"; Molecules, vol. 17, No. 2; Feb. 20, 2012; pp. 2030-2048 (19 pages).
Database GNPD (Online) MINTEL; Jun. 21, 2012; "DHA. Ginko Biloba Leaf & Astaxanthine Supplement"; retrieved from www.gnpd.com (2 pages).
Yamashita et al; "Astaxanthin-rich green alga Haematococcus pluvialis enhanced extreme endurance performance and improved heart rate recovery in exercised rats"; The FASEB Journal; vol. 30, No. 1 supplement; Apr. 1, 2016 (3 pages).
Sawaki, K. et al; "Sports Performance Benefits from Taking Natural Astaxanthin Characterized by Visual Acuity and Muscle Fatigue Improvement in Humans"; Journal of Clinical Therapeutics & Medicines; vol. 18, No. 9, 2002; pp. 1085-1100; English translation (12 pages).

* cited by examiner

*Primary Examiner* — Qiuwen Mi
(74) *Attorney, Agent, or Firm* — Venable LLP; Jeffri A. Kaminski

(57) ABSTRACT

Nutritional supplement compositions for improving cardiovascular efficiency are disclosed. A nutritional supplement composition can include astaxanthin derived from *Haematococcus pluvialis* Extract blended with carrier oils and antioxidants. Related processes are also disclosed.

10 Claims, No Drawings

NUTRITIONAL SUPPLEMENTS AFFECTING CARDIOVASCULAR EFFICIENCY

This application is a U.S. National Stage application of PCT/CN2017/104837, filed Sep. 30, 2017 and published on Apr. 12, 2018 as WO 2018/064966, which claims the benefit of U.S. Provisional Application No. 62/404,853, filed Oct. 6, 2016, the contents of which are hereby incorporated by reference in their entireties.

TECHNICAL FIELD

The present disclosure relates generally to the field of nutritional treatments and supplements. More particularly, the present disclosure relates to nutritional treatments and supplements for, among other things, improving cardiovascular efficiency.

BACKGROUND

Nutritional supplements are routinely used to improve health and/or physical performance. While nutritional supplements may be tailored to provide specific health and/or performance benefits, relatively few supplements provide such benefits specifically by improving the efficiency of the cardiovascular system.

DETAILED DESCRIPTION OF THE EMBODIMENTS

The present disclosure relates to nutritional treatments and supplements, and more particularly, to nutritional treatments and/or supplements that improve cardiovascular efficiency of an individual. The following detailed description of various embodiments is not intended to limit the scope of the present disclosure, but is merely representative of various embodiments.

Amounts, concentrations, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, an amount of from 1 mg to 200 mg should be interpreted to include not only the explicitly recited limits of 1 mg and about 200 mg, but also to include individual amounts such as 2 mg, 3 mg, 4 mg, and sub-ranges such as 10 mg to 50 mg, 20 mg to 100 mg, etc. Unless otherwise stated, all ranges include both endpoints. The terms "cardiovascular efficiency" and "cardiac tonic" are defined as described in Example 1 and elsewhere in the detailed description.

Nutritional supplements disclosed herein may include astaxanthin derived from *Haematococcus pluvialis* (*H. pluvialis*).

For example, in some embodiments, a nutritional supplement may include astaxanthin from *Haematococcus pluvialis*, a freshwater species of Chlorophyta from the family Haematococcaceae. This species is well known for its high content of the strong antioxidant astaxanthin. The high amount of astaxanthin is present in the resting cells, which are produced and rapidly accumulated when the environmental conditions become unfavorable for normal cell growth. Examples of such conditions include bright light, high salinity, and low availability of nutrients. The bright red color of *H. pluvialis* is caused by astaxanthin which is believed to protect the resting cysts from the detrimental effect of UV-radiation, when exposed to direct sunlight.

In some embodiments, the extract of *H. pluvialis* (describe Astazine spec) is used as a nutritional supplement providing astaxanthin. In a embodiment, a nutritional supplement comprising: *Haematococcus pluvialis* Extract, edible carrier oil, and natural antioxidant.

In some embodiments, the edible carrier oil is Medium Chain Triglyceride.

In some embodiments, the natural antioxidant is D-alpha tocopherol.

In some embodiments, the extract of *H. pluvialis* (describe Astazine spec) is used as a nutritional supplement providing astaxanthin between 1 mg and 200 mg, between 40 mg and 200 mg; between 70 mg and 200 mg; between 100 mg and 200 mg; between 150 mg and 200 mg; between 15 mg and 150 mg; between 15 mg and 100 mg; between 15 mg and 50 mg, between 40 mg and 130 mg; or between 40 mg and 75 mg of astaxanthin derived from *H. pluvialis* material.

In addition to astaxanthin from *H. pluvialis* material, some nutritional supplements disclosed herein may include one or more of the following ingredients: green tea, green tea extract, quercetin, cyanidin-3-glucoside, (C3G), curcumin/turmeric, boswellia, or hyaluronic acid.

For instance, in some embodiments, a nutritional supplement (e.g., a nutritional supplement packaged for single use) includes C3G in an amount of between 5 mg and 400 mg, between 50 mg and 400 mg, between 75 mg and 400 mg; between 125 mg and 400 mg, between 25 mg and 200 mg; between 25 mg and 100 mg; between 25 mg and 75 mg; or between 75 mg and 125 mg.

In some embodiments, a nutritional supplement (e.g., a nutritional supplement packaged for single use) may include green tea extract in an amount of between 5 mg and 150 mg. In some embodiments, the amount of green tea extract in the nutritional supplement may be between 15 mg and 50 mg.

In some embodiments, the amount of hyaluronic acid in a nutritional supplement may be between 5 mg and 150 mg. In some embodiments, the amount of curcumin/turmeric in a nutritional supplement may be between 15 mg and 250 mg. In some embodiments, the amount of quercetin may be between 1 mg and 200 mg. In some embodiments, the amount of boswellia in a nutritional supplement may be between about 1 mg and 100 mg.

In some embodiments, a nutritional supplement may be formulated as a liquid capsule or soft gel capsule. For example, in some embodiments, ingredients of the nutritional supplement may be mixed into a base liquid or oil for encapsulation. In some embodiments, the liquid or soft gel capsules may be between 1 mg and 1,000 mg in weight. In some embodiments, the nutritional supplement may be packaged for single use.

In some embodiments, the nutritional supplement may exhibit cardiovascular properties. Stated differently, in some embodiments, the nutritional supplement is effective for improving cardiovascular efficiency when administered to a healthy adult. For example, in some embodiments, consumption of the nutritional supplement may cause a decrease in heart rate during sub maximal exercise or physical activity of more than 1%, 2%, 3%, 4%, 5%, 6%, 7%, 8%, 9%, or 10%.

In some embodiments, the nutritional supplement is effective for decreasing heart rate at aerobic threshold and anaerobic threshold systolic when administered to a healthy adult. For example, in some embodiments, the nutritional supplement may decrease average heart rate between 5-20 beats per minute and/or 10-15 beats per minute in a healthy adult. Thus, the nutritional supplement may provide one or more health benefits associated with improvement of cardiovascular efficiency.

In some embodiments, use any one of the nutritional supplement mentioned above in preparing drugs promoting a cardio tonic effect or improving cardiovascular efficiency is provied.

Example 1

Experimental Design

A study was conducted to evaluate the effect of using a nutritional supplement capsule that includes astaxanthin from *H. pluvialis*. More particularly, 12 mg of astaxanthin was supplemented for 8 weeks in healthy subjects. More particularly, the astaxanthin nutritional supplement was a blended combination that included the ingredients set forth in Table 1, which also sets forth the amount of each ingredient in the same table.

TABLE 1

| Ingredient | Amount |
| --- | --- |
| *Haematococcus pluvialis* Extract | 50% |
| Edible MCT Oil (Medium Chain Triglyceride) | 48% |
| D-alpha Tocopherol | 2% |

By way of background, in athletes, astaxanthin supplementation for 4 weeks has been shown to improve various measures of athletic performance at relatively high intensities of exercise. For example, astaxanthin supplementation reduces reduce lactic acid accumulation following 1200 m of high-intensity running and leads to significant improvements in power output and faster completion of a high-intensity 20 km cycling time trial.

Our experiment assessed the effects of 8 weeks of astaxanthin supplementation (12 mg/day) on cardiorespiratory function during higher and lower intensity exercise in healthy subjects.

Using a double-blind parallel design, 28 healthy subjects (male=14, female=14, age=42) were supplemented for 8 weeks with 12 mg/day of AX (*Haematococcus pluvialis* algal extract) or a placebo. Before and after the supplementation period, subjects performed a maximal running test (VO2max on a treadmill) and a maximal cycling test (watts on a cycle ergometer).

Results

There was no improvement in high-intensity exercise conditions, including maximal oxygen uptake (VO2max while running) or maximal power output (watts while cycling) with astaxanthin supplementation. Interestingly, and unexpectedly, subjects in the astaxanthin group showed a significant ~10% lower average heart rate at submaximal running intensities (at both aerobic threshold and anaerobic threshold) compared to placebo, suggesting a profound "cardiotonic" effect of astaxanthin supplementation with superior metabolic efficiency at submaximal aerobic endurance intensities, but not at maximal efforts.

In short, supplementation with 12 mg/day of astaxanthin for 8 weeks reduced heart rate at submaximal endurance intensities where average heart rates are ~137 bpm (aerobic threshold) to ~146 bpm (anaerobic threshold), but not at higher "peak" intensities (e.g. 152 bpm during cycling time trial or 166 bpm at peak running VO2max). These results were unexpected and represent a new invention whereby astaxanthin supplementation may be considered to be a beneficial ergogenic aid for long-distance and ultra-distance endurance athletes (e.g. marathon runners, Ironman triathletes, and ultra-runners/cyclists), but not necessarily for athletes competing in shorter distance higher intensity efforts. In addition, these data also unexpectedly suggest another invention whereby astaxanthin supplementation elicits a general "cardiotonic" effect that may benefit non-athletic populations including elderly subjects and those with cardiac complications including post-myocardial infarction, heart failure, statin usage, mitochondrial dysfunction, chronic fatigue, and related conditions.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Example 2

Formula 2: soft capsule (Table 2) prepared from a natural astaxanthin-containing extract from *H. pluvialis* algae (containing 1% of astaxanthin).

TABLE 2

| Ingredient | Content |
| --- | --- |
| *Haematococcus pluvialis* extract | 100 mg |
| Edible oil | 250 mg |
| Green tea extract | 150 mg |

Example 3

Formula 3: soft capsule (Table 3) prepared from a natural astaxanthin-containing extract from *H. pluvialis* algae (containing 20% of astaxanthin).

TABLE 3

| Ingredient | Content |
| --- | --- |
| *Haematococcus pluvialis* extract | 40 mg |
| Edible oil | 260 mg |
| Quercetin | 200 mg |

Example 4

Formula 4: soft capsule (Table 4) prepared from a natural astaxanthin-containing extract from *H. pluvialis* algae (containing 10% of astaxanthin).

TABLE 4

| Ingredient | Content |
| --- | --- |
| *Haematococcus pluvialis* extract | 150 mg |
| Edible oil | 450 mg |
| Cyanidin-3-glucoside(C3G) | 400 mg |

Example 5

Formula 5: soft capsule (Table 5) prepared from a natural astaxanthin-containing extract from *H. pluvialis* algae (containing 20% of astaxanthin).

TABLE 5

| Ingredient | Content |
| --- | --- |
| *Haematococcus pluvialis* extract | 20 mg |
| Edible oil | 230 mg |
| Curcumin/turmeric | 250 mg |

Example 6

Formula 6: soft capsule (Table 6) prepared from a natural astaxanthin-containing extract from *H. pluvialis* algae (containing 10% of astaxanthin)

TABLE 6

| Ingredient | Content |
| --- | --- |
| *Haematococcus pluvialis* extract | 120 mg |
| Edible oil | 280 mg |
| *Boswellia* | 100 mg |

Example 7

Formula 7: soft capsule (Table 7) prepared from a natural astaxanthin-containing extract from *H. pluvialis* algae (containing 20% of astaxanthin).

TABLE 7

| Ingredient | Content |
| --- | --- |
| *Haematococcus pluvialis* extract | 100 mg |
| Edible oil | 250 mg |
| Hyaluronic acid | 150 mg |

54 healthy subjects (male=30, female=24, age=39) were supplemented for 8 weeks with soft capsules of Formula 2 to 7 (containing *Haematococcus pluvialis* algal extract), and 9 healthy subjects for each group. Before and after the supplementation period, subjects performed a maximal running test (VO2max on a treadmill) and a maximal cycling test (watts on a cycle ergometer). Body composition was also measured by bioelectrical impedance analysis, including body weight, body fat percentage, and basal metabolic rate.

The running VO2max assessment was designed for participants to reach maximal oxygen consumption and voluntary fatigue within 15 minutes. The protocol consisted of a gradual warmup of self-selected easy jogging, followed by progressive increases in speed and incline each minute until exhaustion. Heart rate (beats per minute, bpm) and oxygen consumption (ml/kg/min) were recorded at maximum and at two submaximal levels (aerobic threshold, AeT and anaerobic threshold, AT). The cycling watts assessment was performed as a 20-minute time trial with participants instructed to generate their highest average watts with self-selected workload and target pedal cadence of 90 rpm (range between 80-100 rpm).

Results showed that the nutritional supplement of 7 Formulas were effective for decreasing heart rate at both aerobic threshold (Aet) and anaerobic threshold (AT) systolic when administered to all of healthy subjects. At submaximal exercise intensities, average heart rates of Formula 2 to 7 groups were 134-149 bpm (Aet) to 131-159 bpm(AT), but not at higher "peak" internsities (e.g. ~154-158 bpm during cycling time trial or ~165-172 bpm at peak running VO2max). Submaximal running heart rates were decreased from 1-10% at Aet and 1-9.8% at AT in all of Formula groups, thereof Formula 2 Group (Astaxanthin and Green tea extract) and Formula 4 (Astaxanthin and C3G) Group showed significant lower heart rates than before supplement. Compared before and after the supplementation is administered, aerobic threshold (AeT) average heart rates of subjects decreased 8.9% and anaerobic threshold (AT) average heart rates of subjects decreased 8.0% in Example 2 Group, and Example 4 Group is the best group in these Example 1~7 groups. In Example 4 Group, AeT average heart rates decreased 12.2% and AT average heart rates decreased 9.8%.

Example 8

Formula 8: soft capsule (Table 8) prepared from a natural astaxanthin-containing extract from *H. pluvialis* algae (containing 10% of astaxanthin).

TABLE 8

| Ingredient | Content |
| --- | --- |
| *Haematococcus pluvialis* extract | 120 mg |
| Edible oil | 75 mg |
| D-alpha Tocopherol | 300 mg |
| Cyanidin-3-glucoside(C3G) | 5 mg |

Example 9

Formula 9: soft capsule (Table 9) prepared from a natural astaxanthin-containing extract from *H. pluvialis* algae (containing 20% of astaxanthin)

TABLE 9

| Ingredient | Content |
| --- | --- |
| *Haematococcus pluvialis* extract | 200 mg |
| Edible oil | 225 mg |
| Green tea extract | 50 mg |
| Cyanidin-3-glucoside(C3G) | 25 mg |

Example 10

Formula 10: soft capsule (Table 10) prepared from a natural astaxanthin-containing extract from *H. pluvialis* algae (containing 5% of astaxanthin)

TABLE 10

| Ingredient | Content |
| --- | --- |
| *Haematococcus pluvialis* extract | 240 mg |
| Edible oil | 59 mg |
| Quercetin | 1 mg |
| Cyanidin-3-glucoside(C3G) | 200 mg |

Example 11

Formula 11: soft capsule (Table 11) prepared from a natural astaxanthin-containing extract from *H. pluvialis* algae (containing 10% of astaxanthin)

TABLE 11

| Ingredient | Content |
| --- | --- |
| *Haematococcus pluvialis* extract | 120 mg |
| Edible oil | 65 mg |
| D-alpha Tocopherol | 200 mg |
| Cyanidin-3-glucoside(C3G) | 100 mg |

Example 12

Formula 12: soft capsule (Table 12) prepared from a natural astaxanthin-containing extract from *H. pluvialis* algae (containing 5% of astaxanthin)

TABLE 12

| Ingredient | Content |
| --- | --- |
| *Haematococcus pluvialis* extract | 160 mg |
| Edible oil | 214 mg |
| *Boswellia* | 1 mg |
| Cyanidin-3-glucoside(C3G) | 125 mg |

Example 13

Formula 13: soft capsule (Table 13) prepared from a natural astaxanthin-containing extract from *H. pluvialis* algae (containing 10% of astaxanthin)

TABLE 13

| Ingredient | Content |
| --- | --- |
| *Haematococcus pluvialis* extract | 120 mg |
| Edible oil | 300 mg |
| Hyaluronic acid | 5 mg |
| Cyanidin-3-glucoside(C3G) | 75 mg |

Example 14

Formula 14: soft capsule (Table 14) prepared from a natural astaxanthin-containing extract from *H. pluvialis* algae (containing 5% of astaxanthin)

TABLE 14

| Ingredient | Content |
| --- | --- |
| *Haematococcus pluvialis* extract | 240 mg |
| D-alpha Tocopherol | 205 mg |
| Green tea extract | 5 mg |
| Quercetin | 200 mg |
| Cyanidin-3-glucoside(C3G) | 50 mg |
| Curcumin/turmeric | 150 mg |
| *Boswellia* | 50 mg |
| Hyaluronic acid | 100 mg |

Example 15

Formula 15: soft capsule (Table 15) prepared from a natural astaxanthin-containing extract from *H. pluvialis* algae (containing 20% of astaxanthin)

TABLE 15

| Ingredient | Content |
| --- | --- |
| *Haematococcus pluvialis* extract | 500 mg |
| Edible oil | 100 mg |
| D-alpha Tocopherol | 300 mg |
| *Boswellia* | 100 mg |

48 healthy subjects (male=24, female=24, age=42) were supplemented for 8 weeks with the soft capsule of Formula 8 to 15 (containing *Haematococcus pluvialis* algal extract), and 6 healthy subjects for each group. Before and after the supplementation period, subjects performed a maximal running test (VO2max on a treadmill) and a maximal cycling test (watts on a cycle ergometer).

Results showed that the nutritional supplement of 8 Formulas were effective for decreasing heart rate at aerobic threshold (AeT) and anaerobic threshold (AT) systolic when administered to all of healthy subjects. Formula 11 Group was more effective than other groups. Subjects in the Formula 11 Group (AX, D-alpha Tocopherol, curcumin/turmeric, and cyaniding-3-glucoside) showed a significant ~10% lower average heart rate at submaximal running intensities (at both aerobic threshold and anaerobic threshold) compared to Placebo Group, the nutritional supplement may decrease average heart rate about 18 beats per minute (bpm) and/or 15 beats per minute (bpm) in a healthy adult.

This disclosure should not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

It will be apparent to those having skill in the art that changes may be made to the details of the above-described embodiments without departing from the underlying principles of the present disclosure.

What is claimed is:

1. A method of decreasing heart rate at aerobic threshold and anaerobic threshold systolic when healthy adults exercise, said method comprising administering a composition comprising a nutritional supplement to a subject in need thereof, said composition is prepared by the step of mixing the nutritional supplement into a base liquid or oil for encapsulation; and the nutritional supplement comprising *Haematococcus pluvialis* Extract, Edible carrier oil, and Natural antioxidant, the Edible carrier oil is Medium Chain Triglyceride, and the natural antioxidant is D-alpha tocopherol.

2. The method of claim 1, wherein the nutritional supplement comprising:
    50% *Haematococcus pluvialis* Extract,
    48% Edible carrier oil, and
    2% Natural antioxidant.

3. The method of claim 1, wherein the nutritional supplement comprises between 1 mg and 100 mg of astaxanthin derived from *Haematococcus pluvialis* Extract.

4. The method of claim 1, wherein the nutritional supplement comprising one or more of: green tea, green tea extract, quercetin, cyanidin-3-glucoside (C3G), curcumin/turmeric, boswellia, hyaluronic acid.

5. The method of claim 4, wherein the nutritional supplement comprises green tea extract in an amount of between 5 mg and 150 mg.

6. The method of claim 4, wherein the nutritional supplement comprises quercetin in an amount of between 1 mg and 200 mg.

7. The method of claim 4, wherein the nutritional supplement comprises C3G in an amount of between 5 mg and 400 mg.

8. The method of claim 4, wherein the nutritional supplement comprises curcumin/turmeric in an amount of between 15 mg and 250 mg.

9. The method of claim 4, wherein the nutritional supplement comprises boswellia in an amount of between 1 mg and 100 mg.

10. The method of claim 4, wherein the nutritional supplement comprises hyaluronic acid in an amount of between 5 mg and 150 mg.

\* \* \* \* \*